United States Patent [19]

Bujadoux et al.

[11] 4,366,140
[45] Dec. 28, 1982

[54] ANHYDROUS MAGNESIUM CHLORIDE FROM GRIGNARD REAGENTS

[75] Inventors: Karel Bujadoux, Lens; Jean-Marie Neyer, Bethune; Jean-Pierre Houzeaux, Noeux lex Mines, all of France

[73] Assignee: Societe Chimique des Charbonnages-CdF Chimie, Bully-les Mines Mazingarbe, France

[21] Appl. No.: 249,206

[22] Filed: Mar. 30, 1981

Related U.S. Application Data

[60] Continuation of Ser. No. 66,730, Aug. 15, 1979, abandoned, which is a division of Ser. No. 847,824, Nov. 2, 1977, Pat. No. 4,187,254.

[30] Foreign Application Priority Data

Nov. 9, 1976 [FR] France .................................. 76 33757

[51] Int. Cl.³ ............................................. C01F 5/32
[52] U.S. Cl. ..................................................... 423/498
[58] Field of Search .................. 423/498, 490, 497; 260/665 G, 665 R

[56] References Cited

U.S. PATENT DOCUMENTS

| | | | |
|---|---|---|---|
| 1,992,090 | 2/1935 | Pestalozzi | 423/497 |
| 3,755,478 | 8/1973 | Kamienski | 423/498 |
| 4,187,254 | 2/1980 | Bujadoux | 260/665 G |

FOREIGN PATENT DOCUMENTS 2028105 10/1970 France ........................ 260/665 G
1449139 9/1976 U.S.S.R. ....................... 260/665 G

OTHER PUBLICATIONS

Nesmeyanov et al., (Ed.) *Methods of Elemento-Organic Chemistry*, World Pub. Corp., N.Y., (1967), vol. II, pp. 103–104.

*Primary Examiner*—Brian E. Hearn
*Attorney, Agent, or Firm*—Finnegan, Henderson, Farabow, Garrett & Dunner

[57] ABSTRACT

An organometallic halide having the formula:

$$(RMX)(MX_2)_a(MR_2)_b(MH_2)_c$$

wherein $a \cong 0.45$, $b \cong 0.15$, and $c \cong 0.30$, X is a halogen, R is a hydrocarbon radical, and M is a metal selected from the group consisting of magnesium, zinc, beryllium, and calcium is prepared by a continuous dry process by reacting an organic monohalide RX and a metal M in the form of convex solid grains of a size between 1 and 15 mm. The reaction temperature is lower than the temperature at which decomposition of the organometallic halide RMX begins and at least 10° C. higher than the boiling point of the organic monohalide. The reaction may also take place in the presence of an organometallic derivative comprising a hydroxy group or an enolysable ketone group. The resulting organometallic halide may be used for the synthesis of anhydrous magnesium halide or for the reduction of titanium tetrachloride.

4 Claims, 1 Drawing Figure

U.S. Patent
Dec. 28, 1982
4,366,140
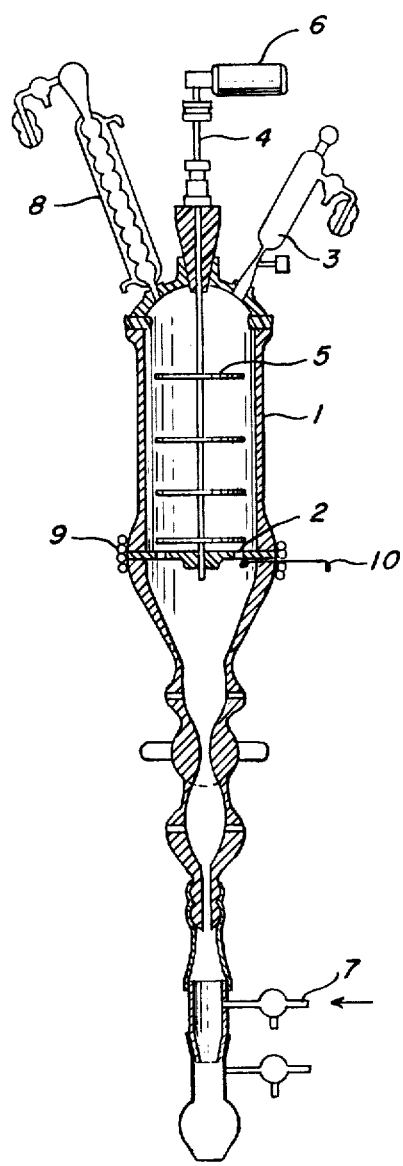

ANHYDROUS MAGNESIUM CHLORIDE FROM GRIGNARD REAGENTS

This is a continuation, of application Ser. No. 066,730, filed Aug. 15, 1979, abandoned which is a division of application Ser. No. 847,824, filed Nov. 2, 1977, now U.S. Pat. No. 4,187,254.

BACKGROUND OF THE INVENTION

The present invention relates to organometallic halides obtained in a novel form and to a process for their preparation. More precisely the invention relates to the synthesis of organic halides of magnesium (the so-called Grignard reagents), zinc (the so-called Blaise reagents), beryllium, and calcium. The invention also relates to the use of Grignard reagents prepared according to this process for the synthesis of anhydrous magnesium halides.

The production of organomagnesium halides by the reaction between magnesium and a hydrocarbon halide in the presence of a solvent such as an ether or a hydrocarbon has long been known. More recently, German Pat. No. 847,595 has described their synthesis without solvent by the reaction between magnesium powder and a liquid hydrocarbon halide. A similar method has been described by Tetrahedron Letters 14, 633 (1962). Likewise, Y. GAULT has published in Tetrahedron Letters 1, 69 (1966) a synthesis without solvent at 0° C. by adsorption at 20 to 200 mm Hg on films of magnesium evaporated under high vacuum. This process requires costly operating conditions and cannot easily be extrapolated to an industrial scale.

A characteristic common to all the aforesaid methods is the use of at least one liquid compound, which results in either the necessity of using the Grignard reagent in the presence of the liquid compound or the necessity of providing a costly supplementary treatment for isolating the Grignard reagent.

Moreover, the formula of Grignard reagents prepared in a solvent has been discussed at length by scientists, and, following the work of JOLIBOIS in 1912 and of SCHLKNK in 1929, the existence of an equilibrium;

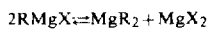

2RMgX⇌MgR$_2$+MgX$_2$ (R is a hydrocarbon radical, X is a halogen atom) is generally acknowledged.

According to SCHLKNK (Berichte der Deutschen Chemischen Gesellschaft 64, 734 (1931)), in the percentage of the form RMgX in the reaction product is generally low; for example, this percentage does not exceed 43% for any of the Grignard reagents including an ethyl, propyl, or phenyl radical and obtained in ether. This of course affects the reactivity of the Grignard reagent towards the numerous chemical substances with which it is able to react. In the following disclosure the percentage of the form RMgX in the product of the Grignard reaction will be referred to as the "purity" of the product.

A first object of the invention is to obtain organometallic halides in a pulverulent form directly utilizable for its subsequent applications. This result, which is achieved by a dry process, has permitted the discovery of organometallic halides of high purity—according to the preceding definition—frequently associated with the corresponding metallic hydride. These particular organometallic halides are novel industrial chemical products. Another object of the invention is the application of these new products to the synthesis of perfectly anhydrous metallic halides.

Additional objects and advantages of the invention will be set forth in part in the description which follows, and in part will be obvious from the description, or may be learned by practice of the invention. The objects and advantages of the invention may be realized and attained by means of the instrumentalities and combinations particularly pointed out in the appended claims.

The accompanying drawing, which is incorporated in and constitutes a part of this specification, illustrates one embodiment of the invention and, together with the description, serve to explain the principles of the invention.

BRIEF DESCRIPTION OF THE DRAWING

The drawing illustrates an apparatus that can be used to carry out the process of producing organometallic halides in accordance with the present invention.

SUMMARY OF THE INVENTION AND DESCRIPTION OF THE PREFERRED EMBODIMENTS

The invention therefore relates firstly to organometallic halides of the formula (RMX) (MX$_2$)$_a$(MR$_2$)$_b$ (MH$_2$)$_c$ in which a≦0.45, b≦0.15, and c≦0.30, X is a halogen, R is an organic radical, and M is a metal selected from the group consisting of magnesium, zinc, beryllium, and calcium. According to the invention, X is any of the fluorine, chlorine, bromine, and iodine atoms; R is selected from the saturated aliphatic (linear or branched), cycloaliphatic, aromatic, unsaturated aliphatic, alkylaryl, arylalkyl, alkoxyalkyl, alkoxyaryl radicals, as well as from heterocyclic radicals, such as pyridyl, furyl, tetrahydrofuryl, thiophenyl, thiazolyl, and quinolyl.

The invention relates secondly to a continuous dry process for the synthesis of the above-mentioned compounds by reaction between an organic monohalide RX and a metal M, wherein the metal is in the form of convex solid grains of a size between 1 and 15 mm and the reaction temperature is lower than the temperature at which decomposition of the organometallic halide RMX begins and at least 10° C. higher than the boiling point of the organic monohalide under the reaction pressure used. It should be noted in particular that the metal must be in molar excess with respect to the monohalide and that the specified reaction conditions provide a reaction of the solid-gas type. In the particular case in which the monohalide is a monofluoride, the process according to the invention is moreover characterized by the fact that the reaction must take place in the presence of an activator, such as bromine, iodine, 1,2-dibromoethane, ethyl bromide, or cobalt chloride.

In the manner which is conventional for the preparation of Grignard reagents, the reaction must take place under an inert and dry gas atmosphere, such as, for example, nitrogen or a rare air gas (e.g., helium, neon, or argon), and with intense agitation. The temperature at which decomposition of the organometallic halide RMX begins is generally available in the literature. For example, this temperature is about 170° C. for the group of alkylmagnesium halides, about 250° C. for the groups of arylmagnesium and arylcalcium halides, and about 200° C. for the group of organoberyllium halides. It should be noted also that the metal M used in the process of the invention is not necessarily very pure as in the former processes using a solvent. It may without disadvantage contain, in the form of impurities or of an alloy, up to 8% by weight of other metals. For example, magnesium may contain at least one of the following metals: copper, iron, manganese, zinc, aluminum, beryllium, and calcium.

An embodiment of the process according to the invention lies in conducting the reaction between the halide RX and the metal M in the presence of a metallic derivative of an organic compound comprising a hydroxy group or an enolysable ketone group. An inventive feature of the process of the invention in this embodiment lies in the fact that, contrary to the process performed in a hydrocarbon solvent, the presence of the organometallic derivative does not modify the yield of the reaction as indicated in British Pat. No. 955,806. Of course, the organometallic halide obtained according to this embodiment of the invention is chemically slightly different from the embodiment described above.

The organometallic derivative that is added to the reaction mixture is preferably an alkoxide of a metal M' selected from the group consisting of magnesium, beryllium, zinc, aluminum, and alkaline-earth metals. It is preferably added in a molar ratio lower than 0.15 relative to the halide RX. The prepared organometallic halide has the formula (RMX) (MX$_2$)a [M'(OR')$_n$]$_d$, in which R' is a hydrocarbon radical, n is the valency of the metal M', a$\leq$0.45, and d$\leq$0.15. When M and M' are the same, the alkoxide may be formed "in situ" by introducing an alcohol R'OH into the reaction mixture.

The main advantage of the process according to the invention lies in the production of organometallic halides in a perfect pulverulent form directly utilizable for subsequent applications. Among other advantages are the improved safety achieved by avoiding the hazards of handling metals such as magnesium in the presence of inflammable solvents, the simplicity and flexibility of the process, the elimination of the hazards of the reaction becoming violent, the absence of any special precautions with respect to the purity of the metal, and the low cost of the products due to the absence of solvent.

Like conventional Grignard reagents prepared in a solvent, the compounds according to the invention show great reactivity towards many kinds of chemical compounds: hydrogen, oxygen, peroxides, carbon oxides, carbonyl organic compounds, ethers, nitrogenous organic compounds, organic halides, organic sulphur compounds, etc. This reactivity results in numerous applications in organic synthesis, in particular for obtaining molecules possessing pharmacological properties. Thus, ethynyl magnesium halides are used for the synthesis of steroids and the manufacture of Vitamin A; tolyl magnesium chloride is used for the synthesis of mephentermine, atropine, and other mydriatic drugs can be obtained by the Ivanov reaction; cyclopentyl magnesium bromide is used for the synthesis of benzhydrol, and, finally, the alkyl mandelates can be obtained by esterification.

Owing to their reactivity with various metallic halides, the compounds of the invention have other interesting applications. Thus, ferrocene and its homologues are prepared by reaction of cyclopentadienyl magnesium chloride with ferrous chloride; silicones are prepared by reaction of organomagnesium halides with silicon tetrachloride. For the purpose of illustrating this type of reaction, an example is the reduction of titanium tetrachloride, which results in products having, after activation by an organoaluminum compound, such as a trialkylaluminum, remarkable catalytic properties with respect to the polymerisation of ethylene. In this example, the process includes suspending a compound of the invention in an anhydrous hydrocarbon solvent having a boiling point preferably higher than or equal to 100° C. The titanium tetrachloride is used pure or in solution in the same solvent so that the reaction mixture has a concentration of titanium between about 100 and about 300 gram-milliatoms per liter. The reaction is carried out with intense agitation at a temperature between −80° and −10° C. The reaction is followed by reheating at an elevated temperature, for example between 100° and 140° C. The reaction product, which then appears in the form of solid grains in suspension in the mixture of titanium tetrachloride and hydrocarbon solvent, is filtered and then washed. It can be kept in the form of powder dried under vacuum and stored under nitrogen, and it has the formula (TiCl$_x$) (MgCl$_2$)$_y$ (RMgCl)$_z$, with 2$\leq$x$\leq$3, y$\leq$1 and 0$\leq$z$\leq$1.

Another application of the invention is the synthesis of totally anhydrous magnesium halide by reacting a Grignard reagent according to the invention with a compound of the formula A-B, in which A is a halogen and B is either hydrogen or a halogen, under such conditions that the reaction is of the solid-gas type. The reaction may take place in accordance with the fluidized bed technique.

Thus, the reagent chosen may be a halogen, for example chlorine, a mixed halogen, for example BrCl, or a hydrogen halide. The majority of these reagents being gaseous at ordinary pressure and temperature, the reaction will be performed under ordinary conditions. However, when the reagent chosen is Br$_2$, BrI or ClI, it is necessary to bring the temperature to the boiling point of the reagent or else to operate under reduced pressure. For the synthesis of magnesium iodide, it is possible to operate in the presence of iodine vapor, but it is more convenient to employ hydrogen iodide as a reagent.

In the case of discontinuous synthesis, the gaseous reagent is brought into the presence of the organomagnesium compound in the form of a mixture with an inert gas, such as nitrogen or a rare air gas, the content of the reagent in the mixture being constantly controlled to permit satisfactory removal of the calories evolved by the reaction, and the duration of the reaction is of the order of some tens of minutes. In the case of continuous synthesis, the gaseous reagent can be passed through a column in counter-current over the organomagnesium powder, while the powder is set in motion with a regular movement, for example, under the effect of a vibratory system. The time of contact between the reagents is then considerably shortened to about a few seconds.

In comparison with the earlier process according to which a gaseous hydrogen halide is allowed to bubble through an ethereal solution of Grignard reagent (French Pat. No. 2,028,105), the solid-gas type reaction according to the invention has many advantages, in particular a reduced reaction time, the absence of the filtering and drying stages, and very great purity of the product obtained. Thus, in the course of the reproducibility tests which have been undertaken, there has always been obtained a pulverulent product with a purity ranging between 96.8% and 99.5% (determined by gravimetric analysis) and a high specific area on the order of 145 m$^2$/g, and comprising in its X-ray diffraction pattern a wide band from 2.60 Å to 2.95 Å.

The following Examples are given to illustrate the preparation and some applications of the organometallic halides according to the invention. These Examples are not restrictive, and various modifications may be made in the operations described without departing from the scope of the invention.

EXAMPLE 1

The synthesis of n-butyl magnesium chloride is carried out in a vertical cylindrical pot 1 shown in FIG. 1. This pot is provided at the bottom with a grid 2 having about three holes of 1 mm diameter per cm$^2$; its capacity is about 750 cm$^3$. Instead of the dropping funnel 3, a metering pump (not shown in the drawing) ensuring a stable flow rate ranging between 1 and 500 ml/h may be used to introduce n-butyl chloride. Before beginning the operation, about 520 g of magnesium (with a purity of 99.8%) in the form of small cylinders 3 to 4 mm in length cut from a wire are charged into the pot. The magnesium could also be in the form of balls, but not in the form of powder, turnings, or chips. Of course, the size of the solid grains of magnesium must be suited to the dimensions of the pot and to the power of the stirrer. Intense friction between the grains is ensured by a mechanical stirrer having a vertical shaft 4 centered in the grid 2, provided with horizontal fingers 5, and driven by a motor 6 allowing a speed of rotation of 500 to 900 r.p.m. A counter-current of dry nitrogen is introduced at the base of the apparatus at 7 to avoid any return of air in the event of leakage, to remove part of the heat of the reaction, and to carry away the gases originating from the secondary reaction;

$$2C_4H_9Cl + Mg \rightarrow MgCl_2 + C_4H_8 + C_4H_{10}.$$

Although the reflux is always slight or nonexistent, a double-acting condenser 8 enables the vaporised n-butyl chloride to flow back. The desired temperature is obtained by heating at the level of the grid 2 by means of a heating band 9 and is controlled by means of a thermocouple 10 inserted in the grid.

By maintaining a grid temperature T of 110° C. and a flow-rate of n-butyl chloride O of 30 ml/h, a yield rate q of 19.3 g/h of a perfectly white powder is recovered. This corresponds to a yield by weight P of 56%. The powder obtained is titrated by acidismetry; there are found 6.15 millimols/g of active functions, whereas pure n-butyl magnesium chloride has 8.55 millimols/g of active functions, which means a purity of 72% for the product obtained.

EXAMPLES 2 TO 9

Using the apparatus described in Example 1, the synthesis of various compounds according to the invention is carried out by varying the nature of the halide RX and, consequently, the temperature T. Table I below records the results of these syntheses using the symbols defined hereinbefore, determination of the purity being effected by acidimetry.

EXAMPLES 10 AND 11

Using the apparatus described in Example 1, the synthesis of n-butyl magnesium chloride is carried out replacing the n-butyl chloride in the dropping funnel 3 and/or in the intake of the metering pump by a mixture of n-butyl chloride and x% by volume of n-butanol to form the corresponding magnesium alcoholate in situ. The results obtained are given in Table II below.

TABLE I

| Example | RX | T (°C.) | Q (ml/h) | q (g/h) | P (%) | Purity (%) |
|---|---|---|---|---|---|---|
| 2 | $C_4H_9Cl$ | 122 | 16.8 | 13.5 | 57 | — |
| 3 | $C_4H_9Cl$ | 138 | 14.5 | 12.8 | 78 | 87 |
| 4 | $C_4H_9Cl$ | 150 | 10.0 | 6.6 | 58 | 95 |
| 5 | $C_4H_9Br$ | 120 | 35 | 50 | 85 | — |
| 6 | $n\text{-}C_3H_7Br$ | 109 | 28 | 12 | — | 71 |
| 7 | $n\text{-}C_5H_{11}Cl$ | 146 | 11.3 | 8.3 | — | 80 |
| 8 | $n\text{-}C_3H_7I$ | 109 | 16.5 | 20.0 | 61 | — |
| 9 | $C_6H_5Br$ | 200 | 5 | 2.5 | 32 | 100 |

TABLE II

| Example | x % | T (°C.) | Q (ml/h) | q (g/h) | P (%) |
|---|---|---|---|---|---|
| 10 | 2 | 122 | 16.5 | 10.3 | 54 |
| 11 | 10 | 124 | 12.3 | 7.5 | 54 |

TABLE III

| Example | Mg % | X % | $T_1$ °C. | y % |
|---|---|---|---|---|
| 2 | 23.3 | 37.6 | 220 | 38.4 |
| 5 | 16.0 | 54.2 | 220 | 24.6 |
| 8 | 13.1 | 72.5 | 190 | 10.2 |

The gravimetric and acidimetric analyses of the powders obtained in this way lead to the following formulae:

$(C_4H_9MgCl)$ $([C_4H_9O]_2Mg)_{0.02}$ $(MgCl_2)_{0.45}$ for Example 10, and $(C_4H_9MgCl)$ $([C_4H_9O]_2Mg)_{0.10}$ $(MgCl_2)_{0.38}$ for Example 11.

EXAMPLE 12

It is now sought to determine precisely the formulae of the powders prepared in Examples 2, 5, and 8 with the aid both of elementary gravimetric analysis and of thermogravimetric analysis. The latter is performed in a Mettler apparatus under a dry nitrogen atmosphere and at a heating rate of 4° C./min. The first loss of weight, which is y % and occurs at the temperature $T_1$, corresponds to the following pyrolysis reactions:

$C_nH_{2n+1}MgX \rightarrow C_nH_{2n} + HMgX$ and $(C_nH_{2n+1})_2Mg \rightarrow 2C_nH_{2n} + MgH_2$.

Moreover, gravimetric analysis permits the determination of the elements Mg and X, the results thereof being reported in Table III above.

Thus, from the general formula (RMgX) $(MgX_2)_a(MgR_2)_b$ $(MgH_2)_c$ of the compounds according to the invention, gravimetric analysis enables the coefficients a and c to be determined and then thermogravimetric analysis enables the coefficient b to be determined. Thus, the following are found:

$(C_4H_9MgCl)$ $(MgCl_2)_{0.272}$ $(MgH_2)_{0.125}$ for Example 2, $(C_4H_9MgBr)$ $(MgBr_2)_{0.145}$ $(MgH_2)_{0.109}$ $(mg[C_4H_9]_2)_{0.116}$ for Example 5, and $(C_3H_7MgI)$ $(MgI_2)_{0.352}$ $(MgH_2)_{0.257}$ $(Mg[C_3H_7]_2)_{0.127}$ for Example 8.

EXAMPLE 13

250 g of the organomagnesium powder obtained in Example 2 are introduced under a stream of nitrogen into a glass column equipped with a stirrer having helical vanes, the dimensions of the column being such that it is about one third filled in this way. Through a double circuit equipped with a flow meter on each gas inlet, 50 l/h of nitrogen and 5 l/h of hydrogen chloride are initially introduced. The reaction, which is very exothermic, starts immediately and takes place in accordance with the fluidized bed technique. As the reaction progresses, the gaseous mixture is enriched with hydrogen chloride until introducing pure HCl at the end of the reaction. The column is then cleared with nitrogen for a long time before emptying it of its contents. The pulverulent product obtained is subjected to gravimetric analysis, which gives the following results:

|  | Mg % | Cl % |
|---|---|---|
| theoretical | 25.5 | 74.5 |
| experimental | 26.2 | 73.3 |

The yield of the reaction is quantitative.

EXAMPLES 14 AND 15

Reproducing the operating conditions of the preceding Example, hydrogen chloride is reacted with the organomagnesium compounds respectively obtained in Examples 5 and 8. There are obtained in this way, with a quantitative yield, pulverulent products of the respective purities of 99.2% and 97.3%, gravimetric analysis of which supplies the following results:

| Example |  | Mg % | Cl % | Br % | I % |
|---|---|---|---|---|---|
| 14 | theoretical | 17.4 | 25.4 | 57.2 | — |
| 14 | experimental | 18.4 | 21.9 | 58.9 | — |
| 15 | theoretical | 13.0 | 19.0 | — | 67.9 |
| 15 | experimental | 13.9 | 20.1 | — | 63.3 |

EXAMPLE 16

87.3 g of the organomagnesium powder obtained in Example 5 are introduced under a stream of nitrogen into a glass column equipped with a stirrer having helical vanes, the dimensions of the column being such that it is about one third filled in this way. Through a double circuit equipped with a flow meter on each gas inlet, 10 l/h of nitrogen and 9.5 l/h of hydrogen bromide are introduced. The reaction, which is very exothermic, starts immediately and takes place in accordance with the fluidized bed technique. After three hours of reaction, the column is cleared with nitrogen before emptying it of its contents. The pulverulent product obtained is subjected to gravimetric analysis, which gives the following results:

|  | Mg % | Br % |
|---|---|---|
| theoretical | 13.2 | 86.8 |
| experimental | 15.2 | 84.6 |

The yield of the reaction is 93%.

EXAMPLE 17

It is now sought to determine precisely the formula of the powder prepared in Example 9 with the aid of thermogravimetric analysis. The latter is performed in a Mettler apparatus under a dry nitrogen atmosphere and at a heating rate of 4° C./min. The powder undergoes, at the temperature of 250° C., a loss of weight of 29.2% corresponding to the following pyrolysis reaction:

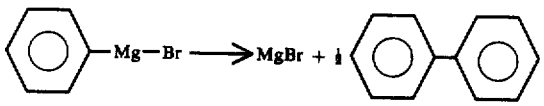

As the purity determined by acidimetry is 100%, $b=c=0$. The termogravimetric analysis therefore permits the determination of coefficient a and the formula of the product:

$(C_6H_5MgBr) (MgBr_2)_{0.45}$.

It will be apparent to those skilled in the art that various modifications and variations could be made in the invention without departing from the scope or spirit of the invention.

What is claimed is:

1. A process for the preparation of anhydrous magnesium halide comprising reacting an organomagnesium halide selected from the group consisting of (1) those having the formula:

$(RMgX) (MgX_2)_a (MgR_2)_b (MgH_2)_c$ wherein $0 \leq a \leq 0.45$, $b \leq 0.15$, and $c \leq 0.30$, X is a halogen and R is an organic radical, and (2) those having the formula:

$(RMgX) (MgX_2)_a [M'(OR')_n]_d$ wherein R and a are defined above, R' is a hydrocarbon radical, M' is a metal selected from the group consisting of magnesium, beryllium, zinc, aluminum, and alkali metals, n is the valency of the metal M', and $d \leq 0.15$ with a compound of formula A-B wherein A is a halogen and B is either hydrogen or a halogen, under such conditions that the reaction is of the solid-gas type.

2. A process according to claim 1, wherein the compound A-B is a hydrogen halide and the reaction takes place under atmospheric pressure and at room temperature.

3. A process according to claim 1, wherein the reaction takes place in accordance with the fluidized bed technique.

4. A process according to claim 1, wherein said magnesium halide preparation is continuous and the time of contact between the reagents is a few seconds.

* * * * *